United States Patent
Jervis et al.

(10) Patent No.: US 8,262,555 B2
(45) Date of Patent: *Sep. 11, 2012

(54) METHOD FOR ADAPTIVE RADIATION TREATMENT OF BREAST TISSUE SURROUNDING A CANCER RESECTION CAVITY OF ARBITRARY SHAPE

(75) Inventors: James E. Jervis, Atherton, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 1286 days.

This patent is subject to a terminal disclaimer.

(21) Appl. No.: 11/932,974

(22) Filed: Oct. 31, 2007

(65) Prior Publication Data

US 2008/0154085 A1   Jun. 26, 2008

Related U.S. Application Data

(63) Continuation-in-part of application No. 10/464,140, filed on Jun. 18, 2003, now Pat. No. 7,322,929.

(51) Int. Cl.
*A61N 5/00* (2006.01)
(52) U.S. Cl. .......................................................... 600/3
(58) Field of Classification Search ................. 600/1–8
See application file for complete search history.

(56) References Cited

U.S. PATENT DOCUMENTS

| | | | |
|---|---|---|---|
| 5,729,583 A | 3/1998 | Tang et al. | |
| 6,251,059 B1 | 6/2001 | Apple et al. | |
| 6,320,935 B1 | 11/2001 | Shinar et al. | |
| 6,402,689 B1 | 6/2002 | Scarantino et al. | |
| 6,556,651 B1 | 4/2003 | Thomson et al. | |
| 7,322,929 B2 * | 1/2008 | Lovoi ............................... 600/3 |
| 7,338,430 B2 | 3/2008 | Lim et al. | |
| 2004/0260142 A1 | 12/2004 | Lovoi | |
| 2006/0241332 A1 | 10/2006 | Klein et al. | |
| 2008/0009658 A1 | 1/2008 | Smith et al. | |

FOREIGN PATENT DOCUMENTS

EP   1050321   8/2000

OTHER PUBLICATIONS

Eric J. Lerner, "Twenty Watts of Terahertz", The Industrial Physicist, p. 9, Apr./May 2003.
"Development of Novel Technologies for in Vivo Imaging", PAR-01-102, May 29, 2001, nih.gov website.
Tearney, Brezinski et al., "In Vivo Endoscopic Optical Biopsy with Optical Coherence Tomography", Science, vol. 276, Jun. 27, 1997, pp. 2037-2039.
Tudor Toma, "Oesophageal Histology Without a Biopsy", The Scientist, Feb. 7, 2001, biomedcentral.com website.
James E. Turner, "Atoms, Radiation, and Radiation Protection", Wiley, 1995.

* cited by examiner

*Primary Examiner* — John Lacyk
(74) *Attorney, Agent, or Firm* — William A. Loginov, Esq.; Loginov & Associates, PLLC (57) ABSTRACT

Radiation treatment methods for breast cancer following resection, both intraoperative and post operative, involve mapping preferably using an electronic x-ray source, and can include rotation of a direction source. By using a very rapid, near-instantaneous method of pathology of tissue margins following resection, the invention carries out intraoperative radiation treatment, preferably with the patient remaining anesthetized. Whether or not radiation is intraoperative, the invention preferably includes a mapping procedure using an electronic source that is progressed through the resection cavity while radiation dose is sensed at one or more points, to determine the shape of the resection cavity.

28 Claims, 8 Drawing Sheets

| Source | Distance | Dose | ms Time/1/$_{10}$Gy |
|---|---|---|---|
| $D_1$ | .5 | 70 | 8.6 ms |
| $D_2$ | 1.0 | 8 | 750 ms |
| $D_3$ | 1.0 | 8 | 750 ms |
| $D_4$ | 1.5 | 2.5 | 2400 ms |
| $D_5$ | 1.75 | 1.7 | 3500 ms |
| $D_6$ | .75 | 20 | 300 ms |

METHOD FOR ADAPTIVE RADIATION TREATMENT OF BREAST TISSUE SURROUNDING A CANCER RESECTION CAVITY OF ARBITRARY SHAPE

This application is a continuation-in-part of application Ser. No. 10/464,140, filed Jun. 18, 2003 U.S. Pat. No. 7,322,929, which is incorporated herein by reference.

BACKGROUND OF THE INVENTION

This invention concerns the treatment of breast cancer or otherwise-sited cancer, and especially an efficient brachytherapy procedure for radiation treatment of tissue surrounding an arbitrarily shaped cavity resulting from following surgical tumor excision. Current brachytherapy methods of treating cancer of the breast, as well as cancer found in other areas of the human body with the patient under anesthesia, include surgical excision of the tumor (with some surrounding tissue) and then typically, after the surgical wound is closed, the patient is sent home pending determination of pathology of the excised tumor margin. Once clean margins are established, a radiation treatment plan is developed and the patient, in a series of later visits, is subjected to radiation treatment in the volume of tissue surrounding the excised tumor. This often involves re-opening the surgical cavity for insertion of an applicator to establish spatial relationships between the cavity and an ionizing radiation source or sources, e.g. radioactive isotopes, used to deliver the radiotherapy. Developing a radiation treatment plan under these circumstances is usually a several-hour process that can require external imaging of the excision cavity to determine its shape and location in the body using external devices such as magnetic resonance imaging, x-ray or CT scanning equipment. Transfer of data is then needed between the imaging equipment and the treatment planning software for preparing a plan of irradiation, with perhaps the need to verify transferred data values to check for errors. Often, the radiotherapy plan is divided into fractions (fractional treatments, the sum of which comprise the total treatment plan) which are separated in time to allow normal tissue to recover between fractions. Diseased tissue does not recover in this manner and therefore tends to be destroyed by the cumulative fractions. The entire prescription plan may require a few days or more to complete.

In the case of breast tumors, because breast tissue has great mobility, applicators are particularly important. The excision cavity may move if not properly supported, and spatial orientation may be lost between fractions. The applicator is therefore usually left inflated throughout the course of treatment, maintaining the spatial relationships built into the treatment plan.

There is also a need for increased precision in delivering radiation to a volume of tissue following surgery, to closely follow a physician's prescription which may vary from location to location within the resection cavity. For example, it may be necessary to reduce the dose to avoid damage to closely adjacent skin during irradiation of breast tissue, and/or to avoid damage to the heart, lungs and bones, while still delivering the full prescribed dose elsewhere. Over-radiation of any tissue is to be avoided as much as possible.

Recent advances in miniature x-ray tubes to replace isotopes for radiotherapy, and advances in rapid determination of resected tumor pathology, taken together, make intraoperative radiotherapy feasible. Regarding advances in pathology determination, see, for example, "Twenty Watts of Terahertz", Eric J. Lerner, The Industrial Physicist, page 9, April/May 2003. See also "Development of Novel Technologies for In Vivo Imaging", PAR-01-102, May 29, 2001, nih.gov website; "In Vivo Endoscopic Optical Biopsy with Optical Coherence Tomography", Tearney, Brezinski, et al., Science, Vol. 276, Jun. 27, 1997, pp 2037-2039; "Oesophageal Histology Without a Biopsy", Tudor Toma, The Scientist, Feb. 7, 2001, biomedcentral.com website; "Determination of Spatial Location and Pathology of Breast Lesions using Proton MRS", imrr.org website; "Multiphoton Excitation Microscopy of Human Skin in Vivo: Early Development of an Optical Biopsy", Barry R. Masters and Peter T. C. So, optics.sgu.ru website. Although the invention contemplates instant pathology supporting an intraoperative procedure, it should be understood that the invention also encompasses a procedure with delivery of radiotherapy following resection after an interval of up to a few weeks rather than as an intraoperative procedure.

Determination of pathology of tissue at the excision site is information the physician uses to determine whether further excision of tissue is required, or if the next step in treatment is radiation planning and delivery. The determination of a treatment plan depends on obtaining information on the shape and location of the excision cavity and any need to avoid damage to other areas of tissue (such as the skin, the chest wall, bones, lungs and heart). The planning process also requires that the emission characteristics of the radiation source be known. With this information, a therapy plan can be developed.

Proxima Therapeutics has developed a program for radiation treatment following tumor excision. In this procedure a breast tumor is excised, then a balloon applicator is inserted into the excision cavity (often through a new incision at the time of tumor excision or up to several weeks later). The applicator is expanded and the incision is closed except for a pigtail or spigot extending out of the breast for later use. At a later date, following determination of pathology, if no further excision is indicated, the patient returns for radiation treatment via the applicator. The Proxima applicator balloons are not capable of changing shape to accommodate irregularly-shaped cavities. The applicator balloons can be filled to the appropriate size for the particular cavity, but beyond this size variation adjustment is not possible. The surgeon therefore needs to cut as nearly matching an excision cavity as possible to enable the proper use of the device. This is often difficult.

With the applicator in the excision cavity and filled, the patient's breast is imaged by exterior imaging equipment. This imaging not only determines the size and location of the inflated applicator within the breast excision cavity, but also enables the physician to look at any gaps between the applicator and the tissue at the boundaries of the excision cavity. If the applicator/tissue contact is sufficient, the physician uses a table to look up the needed dwell time for the diameter of the applicator and for the particular activity of the radio isotope source, which is known. The ionizing radiation source, i.e. an iridium ($^{192}$Ir) wire on the end of a stainless steel guide wire, is inserted into the middle of the applicator for the prescribed duration.

The Proxima procedure is based on a known geometry, e.g. a spherical shape of the applicator and cavity, and ideally, a substantially uniform isotropic iridium source. The equipment is not adaptable to an irregularly-shaped excision cavity, nor to prescription plans where skin, bone or other sensitive structures lie within the prescribed target tissue region. Moreover, the applicator and procedure are not useful for smaller-sized tumors, because of unacceptable surface-to-depth ratio of radiation dose at near ranges of the radiation source.

From the foregoing, it can be seen that there is a need to accommodate arbitrary resection cavity shapes and small cavities, to eliminate unnecessary patient or equipment transport for imaging, and easily to adjust delivered dose locally in order to spare sensitive tissue structures while treating diseased tissue adequately.

The following patent has some relevance to the present invention: European Patent Application EP1050321.

SUMMARY OF THE INVENTION

By the procedures of the present invention, the need for external imaging is eliminated and radiation treatment is adapted to target tissues surrounding arbitrarily shaped cavities with local dose control. Such a procedure may be applied intraoperatively, or may be applied post-operatively over a fractionated course of treatments.

During brachytherapy, the treatment cavity needs to be held open so as to establish and maintain distances between the target tissue and the radiation source or sources. An arbitrary resection cavity may be accommodated by use of a weak elastic balloon on the applicator, and low or at most, moderate inflation pressure. A material for such a balloon might be, for example, silicone rubber of such a thickness that inflation causes the balloon to fill and open the available cavity space, perhaps reshaping somewhat as tissue resistance balances inflation pressure and balloon strength, but without materially forcing the cavity to conform to a preselected balloon shape. Alternatively, the balloon might be of a very thin inelastic material like PET and of such volume that the cavity is filled at low or moderate pressure, but with balloon wall folds or overlaps randomly. Either sort of balloon can accommodate, within a reasonable range, arbitrary cavity geometry or features in the cavity surface. In such a circumstance, so long as external forces on the tissues don't change, the cavity shape should remain substantially constant for the duration of the prescribed radiotherapy. For purposes of radiotherapy according to this invention, guides should be provided within the applicator balloon for sources and radiation sensors, preferably on the balloon surface, as well as on what might be termed a central axis (allowing for the fact the cavity is random and there may be no true axis).

A treatment plan is calculated starting from three dimensional applicator/cavity mapping data and the treatment plan is executed preferably using the same applicator, the same applicator position and the same ionizing radiation sources as are used in the mapping, controlled by a processor. In a sense, the mapping step of the inventive procedure comprises a low-dose "trial treatment", providing accurate, useful data, with verification of the effects of each of the radiation sources and dwell positions in the applicator guides, including areas where radiation needs to be modulated or is not to be delivered at all, thus enabling optimized planning and enabling accurate execution of the treatment plan subsequently.

Dose variability, in a practical sense, can be enabled by use of miniature x-ray sources at the ends of cables or catheters such that the sources can be manipulated from without the patient, much like isotopes are used with afterloaders. Unlike isotopes, however, such sources further lend themselves to variable voltage operation which determines penetration depth, and variable current which can determine dose intensity (as can emission dwell time). In contrast, isotopes cannot be controlled in any practical sense. Some x-ray sources of this sort can also be turned on and off at will. X-ray tubes in general do not emit isotropically, but often emit uniformly in all radial directions perpendicular to the tube axis. Alternatively, x-ray tubes can also be fashioned to emit only over limited solid angle aimed in a particular direction. Such x-ray tubes are described in, e.g., U.S. Pat. No. 5,729,583, and in "Atoms, Radiation, and Radiation Protection", James E. Turner, Wiley, 1995. Such a directional source can be manipulated within source guides along the guide axis, or can be rotated within the guide in a controlled manner. Both translation and rotation can be continuous or intermittent. Similar solid-angle emissions from a radiation source can also be obtained by shielding techniques. (See co-pending patent applications Nos. 11/323,346 and 11/471,013.)

Rotating x-ray sources are well known, but generally the methods used to effect rotation are directed to large, external x-ray sources, not miniature sources. Miniature sources are usually connected to a high-voltage electrical and/or optic cable, more or less in the manner of a source on the end of a catheter. The problems which would be encountered in making rotating high-voltage or optic connections are substantial. It is far easier to use solid cable connections and twist the cable rotationally, perhaps increasing cable length somewhat to accommodate sufficient accumulated rotation, or to resort to oscillatory rotation such that the cable is first wound and then unwound within a more limited range, but still sufficient to accommodate the rotational requirements of the treatment plan.

In order to use a directional source effectively in an arbitrary cavity, the cavity must be established in a configuration that can be maintained for the duration of the radiotherapy prescription, and then mapped such that optimized dose planning can proceed (or re-mapping can take place, accompanied by recalculating the delivery procedure or by real-time monitoring of dose received and real-time adjustment accordingly). If the radiotherapy prescription is carried out intraoperatively, the apparatus and procedure of the invention not only greatly improve accuracy in radiation treatment, but also subject the patient to far less discomfort and trauma as compared to typical procedures. By the disclosed procedure the patient, while anesthetized in the operating room, is operated on to remove the tumor, the tumor is investigated as to pathology, by a very rapid process, decision is made as to any need for further excision (which is done if needed), the physician prescribes radiation dosage for a volume of tissue surrounding the excision cavity, the shape of the cavity is mapped and recorded by internal measurements, calculations of radiation to be delivered at various sites in the cavity are made by use of the mapping data to thus prepare a treatment plan, and the treatment plan is carried out, all without waking or moving the patient, and all within a reasonable time. In the fractionated procedure, on the other hand, the patient is sent home between the various steps and fractions as is either convenient or efficacious for the duration of the radiotherapy.

In a preferred form of the invention, the procedure is applied to treatment of breast cancer. The tumor is excised from the breast, producing an excision cavity. Next, pathology is determined, and further excision is made in the breast cavity if needed. The applicator is then placed within the cavity and expanded to substantially fill the excision cavity, so that the peripheral guides are placed at walls of the cavity adjacent to a target volume of breast tissue to be treated with radiation, such volume having been adjacent to the removed tumor, and a generally central guide is positioned within the balloon volume. The excision cavity is then mapped using at least one x-ray source, either a radially uniform source or a directional source, and at least one sensor, the radiation source(s) being inserted into the peripheral guides (simultaneously or sequentially), and a radiation sensor being placed into a central guide (see below for a procedure with reversed sensor/source positions). The excision cavity of the breast is mapped by moving the sources and sensor through the guides, preferably in a manner such that the data on dose received are gathered collectively for what are substantially planes transverse to the central guide, determining dose at the sensor for each of the sources in turn at a plurality of locations along the guides, those locations being sufficient to substantially define the shape of the walls of the cavity. Dose received at the sensor for each source at each location is calculated into a distance from the source to the sensor, thus enabling a three dimensional wire-frame type map or model to be generated. If a helical pattern of data collection, or for that matter a random pattern of collection for mapping is preferred, the dose planning optimization algorithm must be conformed such that a useful plan results.

Such an algorithm is called a reverse planning algorithm. In principle, x, y, z (or other) coordinates must be established, preferably in relation to the (substantially) central guide within the applicator balloon. Sensors are placed on the skin as described above, as well as at the chest wall (by needle methods), and after insertion and inflation of the applicator and its balloon, at least one sensor within the central guide. A source or sources of known emission characteristics are inserted into the peripheral guides within the balloon and activated sequentially, then stepped in position according to the plan pattern chosen. Dose data are collected from each source position adjacent to the balloon surface at each corresponding sensor position. Because the emission decay characteristics of the source(s) is known, the dose data can easily be converted to the distances between the activated source at each position and the sensor in its corresponding position. In total, an over constrained data set will result on which statistical methods can be applied to produce an accurate three dimensional spatial representation of the resection cavity shape and size (and with the data from the skin and chest wall sensors, the cavity location). The therapist then looks at each node of the cavity map and assigns a prescription dose for that node. Since the data set for the total dose at each node contains a contribution from all other nodes, the algorithm can then optimize the activation dwell times at each position in each source guide, varying source voltage and current as well in order to produce the best fit to the prescription plan. If necessary, a number of trials can be carried out interactively within the computer to produce the best fit.

In a preferred embodiment, the sensors located outside the breast volume to be treated, on the skin surface and at the chest cavity wall (by needle), are monitored during mapping so as to similarly locate the cavity within the breast.

The physician prescribes radiation treatment for the breast volume which surrounded the excised tumor, which is translated to each node of the wire-frame representation of the treatment. From this prescription and from the derived three-dimensional map of the excision cavity, a radiation treatment plan is calculated for the volume to be treated immediately surrounding the excision cavity. The location of the cavity is important and the location data are used to avoid damaging radiation at the skin and at the chest wall. Computer software determines the treatment plan based on all this geometry and incorporating known source characteristics, which in the case of an x-ray tube, can be varied to suit treatment planning needs.

Next, with the applicator remaining in position in the cavity and the balloon expanded as in the mapping step, the radiation treatment plan is carried out via movement (translation and/or rotation in keeping with the treatment plan), repositioning the ionizing radiation sources within the peripheral applicator guides. Appropriate dwell times are used for the various source locations, such that the appropriate dose of radiation is received in essentially all regions of the volume to be treated, without damaging sensitive areas such as the skin and chest wall. The sensors outside the breast can be used to monitor radiation actually received during the procedure at those sites, and/or as feedback to stop the procedure if excess dose is received or is predicted to exceed the prescribed dose. Equally, a sensor positioned in the (substantially) central guide, as in the mapping step, may be used similarly for control and/or monitoring.

In the description above, the procedure is carried out using a source or sources in the peripheral guides, with the central guide used for a sensor (or sensors). Alternatively, these relationships can be reversed such that mapping is carried out with the source in the central guide, and the sensor(s) used in the applicator during treatment, if any, are in the peripheral guide(s). The description above also describes use of an applicator having a substantially elastic balloon in order to accommodate an arbitrary excision cavity. For the same reasons, the invention is also useful with more traditional, less elastic balloon applicators, and more regular excision cavities.

In another variation, side emitting sources (emitting within a defined solid angle) which are translated along the length of the guides as well as rotated with respect to the applicator and anatomy, can also be used. Again the algorithm must be designed to create an optimized treatment plan using these additional degrees of freedom. This rotational, side emitting embodiment can be particularly advantageous where the source is translated and rotated within a substantially central guide, rather than positioned in peripheral guides. With such an arrangement, when the x-ray tube is modulated as it rotates, and emits in a manner reaching out to or retreating from irregular cavity surfaces and treatment plan requirements. References describing side emitting, miniature x-ray tubes are mentioned above. Side emitters can be used in mapping, so long as orientation is managed and known.

In a preferred procedure, the ionizing radiation sources comprise x-ray sources, variable as to voltage and current, as well as being switchable on/off during treatment, allowing the treatment plan accurately to treat the prescribed volume without damage to sensitive areas. The sensors outside the breast volume to be treated are monitored to verify the accuracy of the procedure, and can actively feed back information to the processor controlling the treatment. With controllable x-ray sources this feedback can be used to reduce depth of penetration of radiation from the x-ray source or sources as needed, including in real time to conform the dose delivered to plan, or for later verification that the prescribed plan was in fact delivered.

It is therefore among the objects of the invention to improve availability and control of radiation treatment of breast cancer and other malignant tumors, primarily by accommodating a wide range of therapeutic situations or what would be counter-indications with current techniques and which would otherwise preclude many patients from the ease and efficacy of brachytherapy. Related objects are the mapping procedure itself, and the treatment using highly controllable x-ray sources, preferably with real-time monitoring using extra-cavity sensors. These and other objects, advantages and features of the invention will be apparent from the following description, considered along with the accompanying drawings.

DESCRIPTION OF PREFERRED EMBODIMENTS

Figure 1:
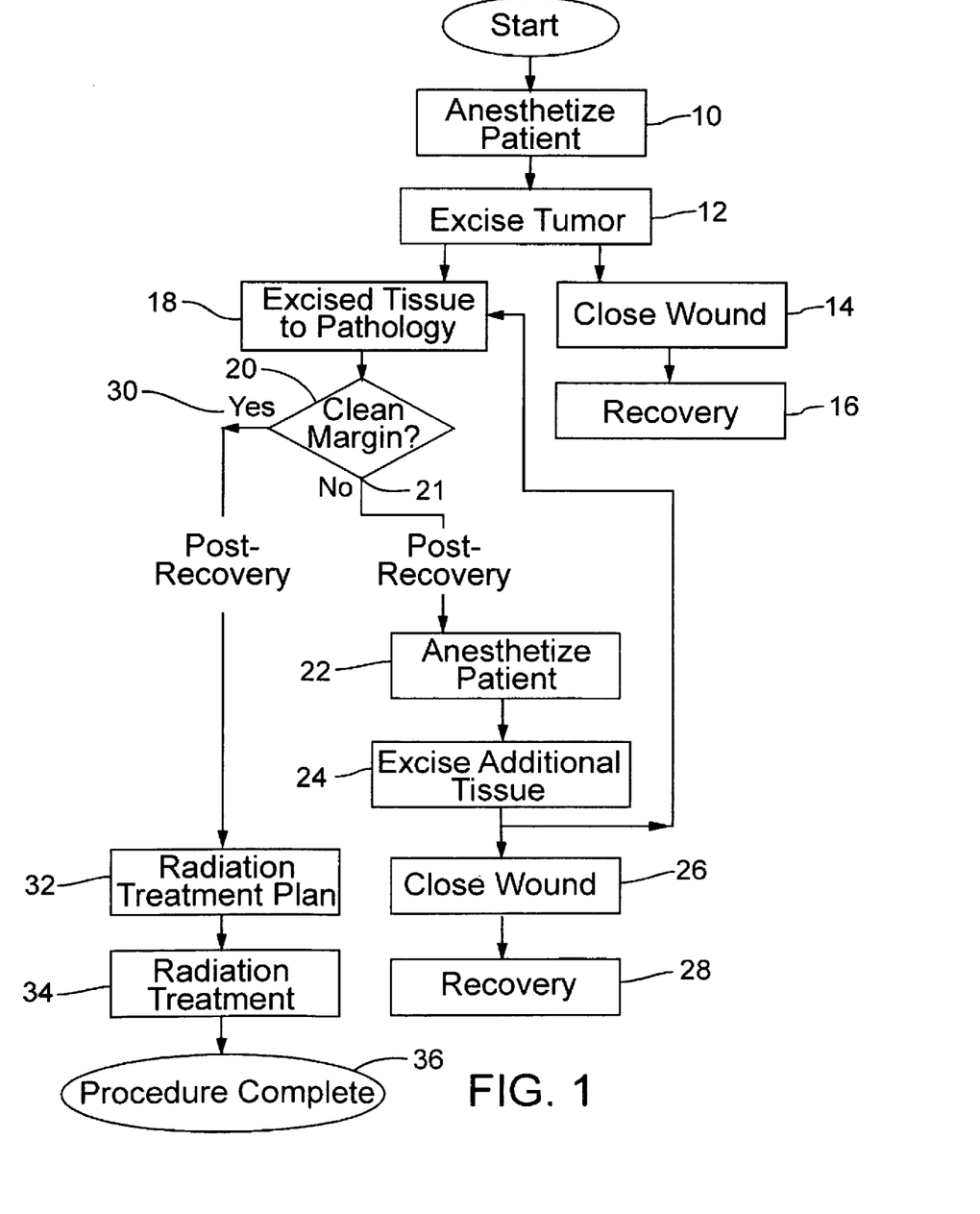
FIG. 1 is a flow diagram showing typical brachytherapy practice after excision of a tumor, where pathology determination is made post-operatively, and is followed by subsequent treatment planning and radiation.

FIG. 1 shows typical brachytherapy practice where pathology of the excised tissue is performed post-operatively, particularly after a tumor has been excised from the breast of a patient; FIG. 1 represents prior art as well as the invention, with further details set out below. The patient is anesthetized as indicated at 10, and the tumor is excised as indicated at 12 in the drawing. Following excision, the surgical wound is closed as noted at 14, and the patient recovers as shown in the block 16 and is sent home. Optionally, a place holding balloon in accordance with the teaching of co-pending provisional patent application No. 60/851,687 may be implanted in the resection cavity before closing, in anticipation of subsequent radiotherapy following satisfactory pathology. The specification of application No. 60/851,687 is included herein by reference in its entirety.

Meanwhile, the excised tissue is sent to pathology as shown at 18, and the pathology of the tissue is determined as to whether there is a clean margin, as indicated at 20. As explained above, this may take some time. Different surgeons apply different standards as to whether a margin is sufficiently clean such that subsequent radiation treatment is judged to be sufficient to remove all remaining microfiche disease which might remain. If the physician decides the pathology of the tissue does not indicate a clean margin, as at 21, then further excision is deemed to be necessary. Thus, in this case, the post-recovery patient is again anesthetized at 22, additional tissue is excised, through the same or a different surgical wound, as at 24, and the excised tissue is again sent to pathology, as indicated by return to the block 18. The surgical wound is closed (block 26), and the patient again recovers from the surgery, indicated at 28, and is again sent home.

Figure 3:
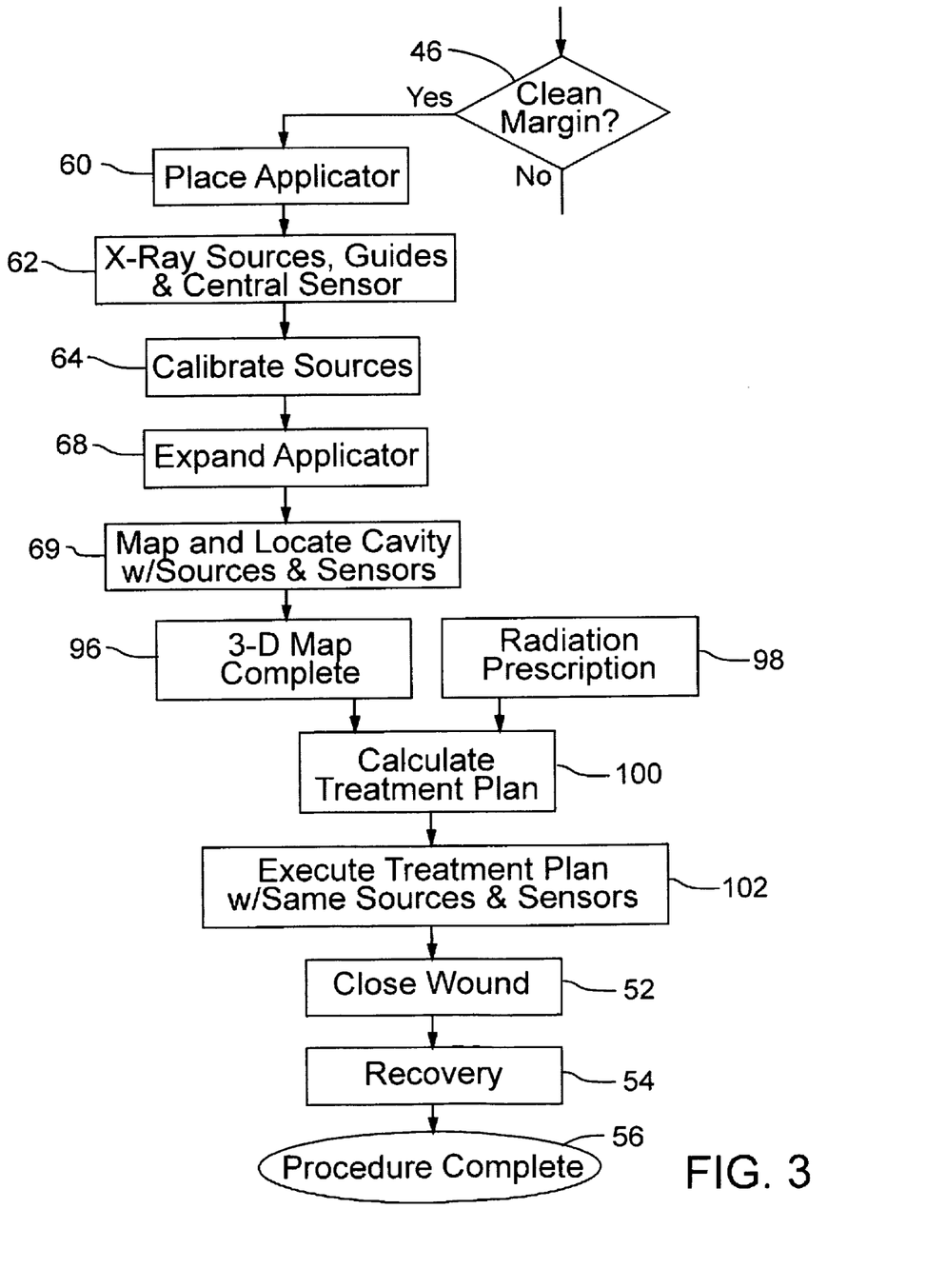
FIG. 3 is a partial flow diagram in greater detail, incorporating a preferred three-dimensional cavity mapping procedure in accordance with the invention, for use with the procedures of FIG. 1 or 2.

If, at the decision block 20, the surgeon decides the excised tissue exhibits a clean margin (30), then a radiation treatment plan is prescribed and calculated, as noted in the block 32 (see FIG. 3 for planning detail). Then the patient is treated with radiation according to the treatment plan, as indicated at 34. If desired, the total treatment may be given in one session or dose. Alternatively, the treatment may be given in fractions as is often done in brachytherapy. At 36 completion of the procedure is indicated. In this traditional invention, the radiation treatment plan is derived from detailed mapping of the cavity as described below with regard to FIG. 8, and a dose prescription which typically involves a standard dose of radiation at a standard prescribed depth in the tissue surrounding the excision cavity in the patient, but with the dose modulated where necessary adjacent to sensitive anatomical structures which lie partially or totally within the standard prescribed depth. Such modulation is discussed below in the descriptions of FIGS. 5, 5A and 5B.

Figure 2:
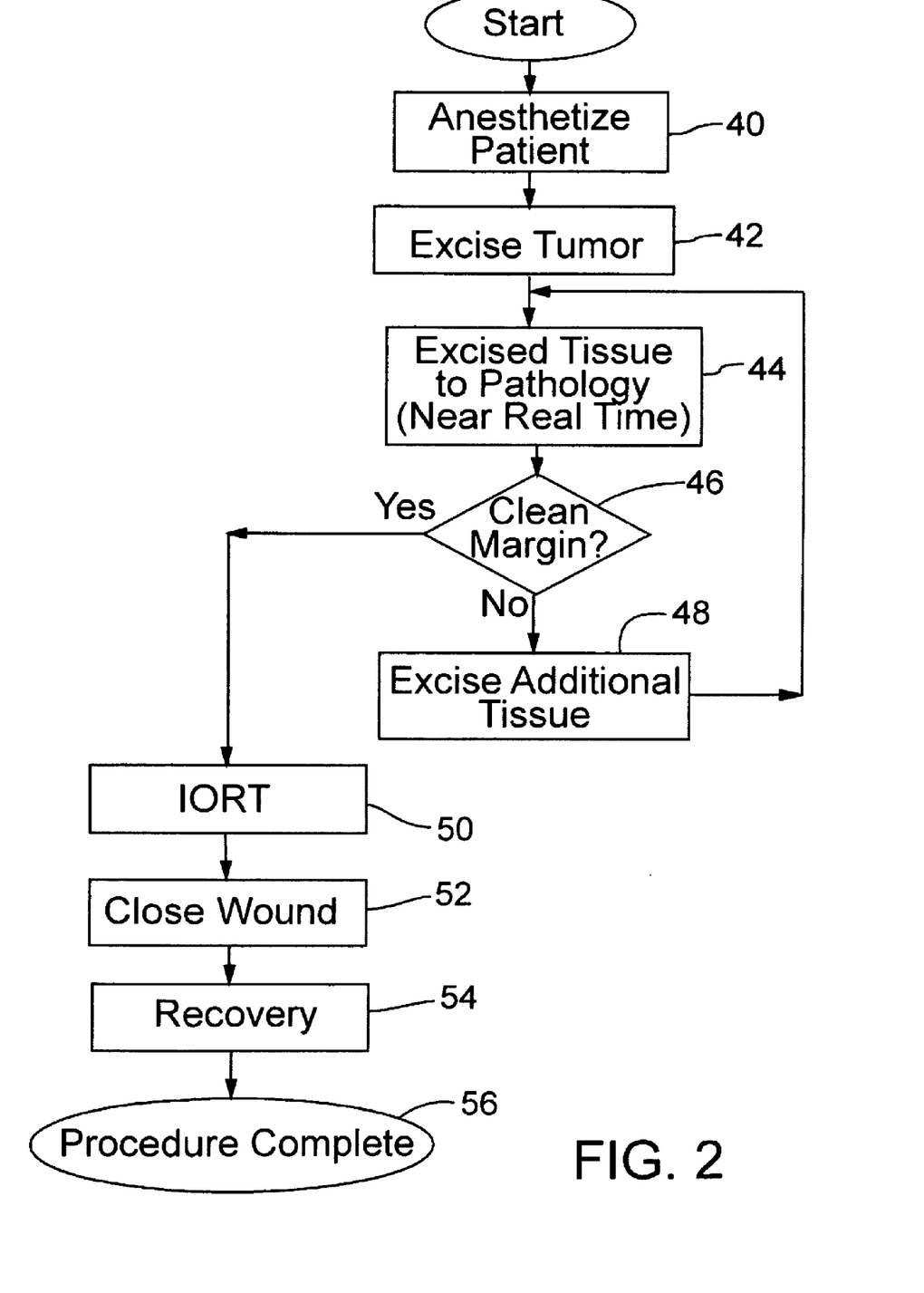
FIG. 2 is a flow diagram outlining an intraoperative procedure which may be used in conjunction with the invention.

FIG. 2 is a flow chart similar to that of FIG. 1, but showing the main elements of a procedure according to the invention where determination of pathology is more or less immediate, and radiation treatment following excision of a tumor is performed intraoperatively. The patient is anesthetized at 40 and the tumor is excised at 42, as in the prior procedure. The excised tissue is taken to pathology (block 44), and as noted in the decision box 46, it is determined through pathology whether the tissue exhibits a clean margin. This is accomplished with a near-real-time method of pathology without waking and preferably without moving the patient.

If it is determined that the excised tissue (or by inference, the wall of the excision cavity) does not exhibit a clean margin, then the surgeon proceeds to excise additional tissue, indicated at 48. This may be through the same or a different surgical incision. With this completed, the additional tissue is examined by the near-instantaneous method of pathology, and if necessary repeated interactively until a clean margin results.

With a clean margin, the process proceeds to IORT, Intra-Operative Radiation Therapy, shown at 50, including calculation of a treatment plan. (See discussion of FIGS. 3 and 8.) After the radiation treatment, the wound is closed (52), the patient is allowed to recover, indicated at 54, and the procedure is complete (block 56).

FIG. 3 is a more detailed flow chart, showing additional steps in mapping the cavity (see discussion of FIG. 8), preparing a treatment plan (see discussion of FIGS. 5, 5A and 5B) and delivering radiation in a preferred radiotherapy procedure according to the invention.

Once a clean margin is determined (as at 20 in FIG. 1 or 46 in FIG. 2), and with an applicator of the invention placed into the excision cavity (intraoperatively or post-operatively as described above) as noted at 60, treatment planning is ready to proceed. The applicator may be a balloon type device or other expandable applicator having guides for receiving sources and/or sensors, preferably for receiving an x-ray sources and sensors placed as described in the summary above. Once the applicator has been placed in the excision cavity, the x-ray sources are inserted into guides which will ultimately be expanded against the walls of the cavity, and a sensor is placed in the central guide, as indicated in the box 62. Then the sources are calibrated (as at 64) with the applicator collapsed and with the sources closely adjacent to the central sensor. This is shown schematically in FIG. 4, the guides containing the sources being shown at 65 and the central guide with the sensor being at 66. The later expanded positions of the guides 66 are shown at 65a, against the wall 67 of the excision cavity. (If preferred, multiple sensors may be positioned peripherally and a single source centrally. The steps which follow may be conformed to the inversion of elements as will be apparent to one skilled in the art.)

With this calibration data taken in the collapsed state as to the radiation emanating from each of the sources as read at the adjacent sensor, differences in the sources and relative values can be determined such that once the applicator is expanded, doses read at the central sensor from each source can be used to calculate distance accurately.

Figure 4:
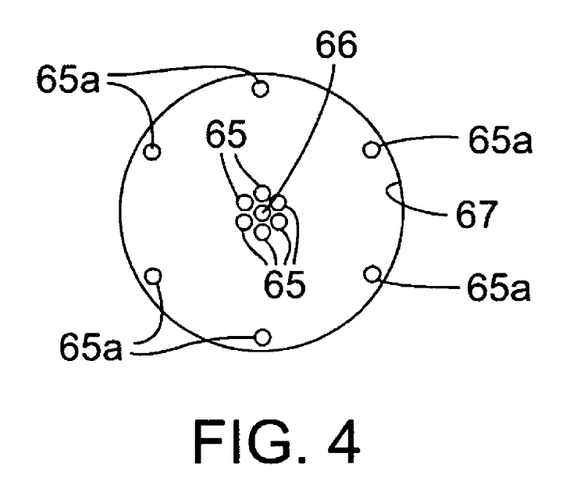
FIG. 4 is a schematic cross-section view of an applicator, the drawing schematically indicating a step for calibrating the radiation source(s) prior to mapping and prior to treatment.

With the sources calibrated, the applicator is expanded as indicated at 68 in the flow chart and at 65a in FIG. 4.

Figure 5:
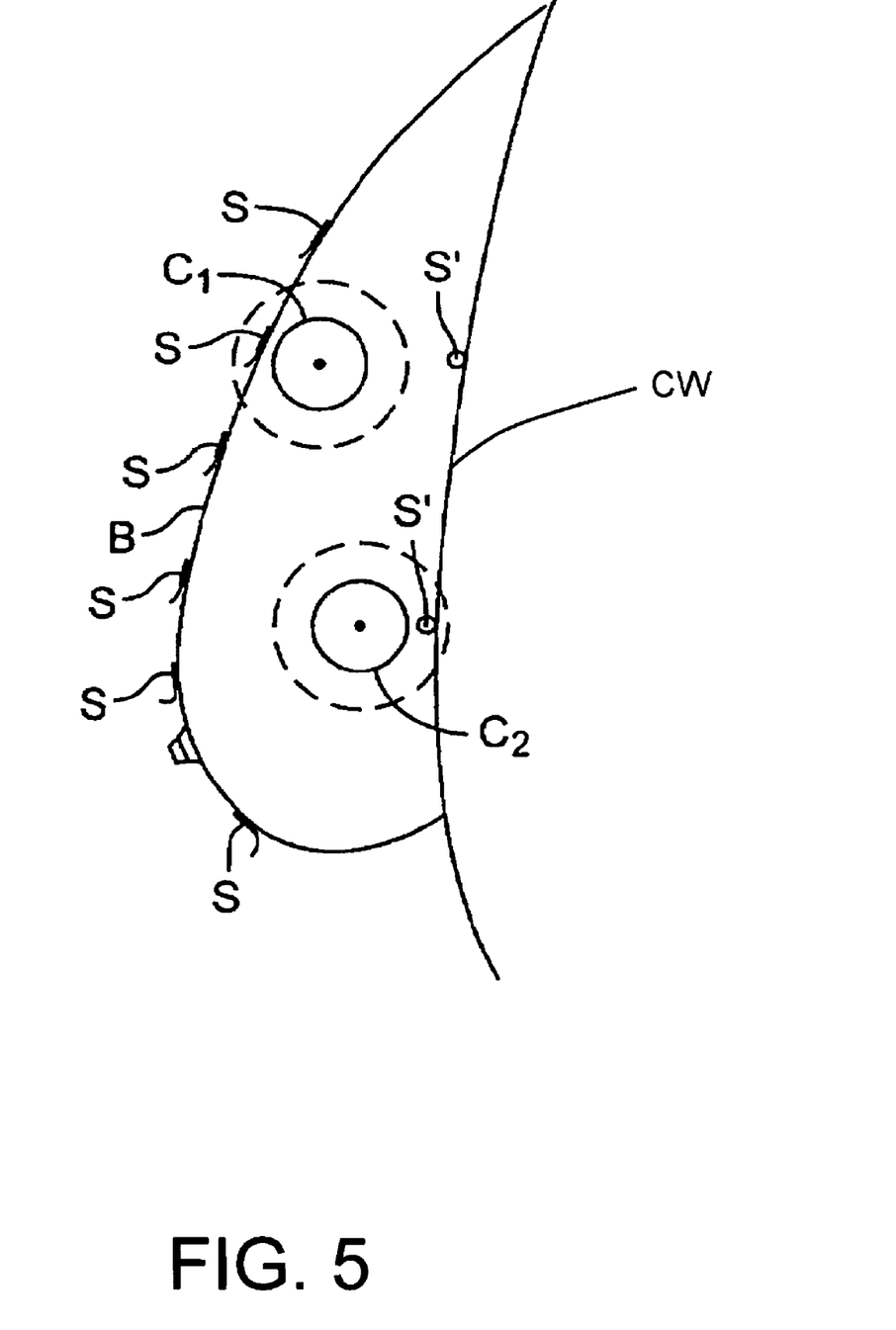
FIG. 5 is a schematic view in sectional elevation indicating several possible locations of excision cavities in a breast, surrounded by a traditional isotropic volume to be treated and indicating depth of prescribed radiation in the volume to be treated, and the intersection of the prescription radiation volume with the skin and chest wall, and also indicating use of sensors on the breast and elsewhere outside the cavity for locating the cavity and for absorbed dose feedback.

The expansion of the applicator locates the x-ray source guides directly against the walls of the excision cavity (FIG. 4), with the sensor guide remaining in a generally central location (66 in FIG. 4). Preferably, additional sensors have been placed at other strategic locations as discussed above: in the case of the breast, on the exterior surface of the breast, and perhaps also at the chest wall, via a needle or needles. These sensors may be used to locate the excision cavity during the mapping step to be described below, as well as providing a means control of the source(s) and possibly emergency shut-off during the radiation treatment, as well as for later verification of treatment to plan. FIG. 5 shows schematically, in the case of a breast B, sensors s located on the exterior surface of the breast, preferably arrayed laterally as well as in vertical separation as shown, and sensors s' inserted via needle at the chest wall CW. This is discussed further below.

With the applicator expanded and the sensor or sensors in place, the three dimensional mapping begins as indicated at 69 in FIG. 3. The patient remains in the same position, and radiation sources, which may be switchable, small x-ray tubes, or isotope sources, are placed in the guides of the applicator. With the radiation sensor located in the generally central guide, the sources and sensor in the guides are pulled back in a series of steps from the distal end of the excision cavity to the proximal end, perhaps through five to ten different longitudinal positions of the cavity (i.e. positions along the length of the applicator guides). In the case of switchable x-ray sources, each source may be switched on for a set, short period of time, and the dose read at the central sensor. Alternatively each source may be switched on at maximum voltage for maximum penetration, and switched off automatically when a preselected dose of x-rays is detected at the sensor. The duration of time is then used to calculate distance, as discussed below in reference to FIGS. 6 and 7. In either event this is done in succession for the plurality of sources placed around the walls of the cavity, e.g. about two to ten sources (different numbers can be used). In this way, a unique reading is obtained for each source position, and this is repeated at the plurality of longitudinal positions in the cavity as noted above. Each dosage value (or time duration) is translatable into a distance, and thus a three dimensional map of the incision cavity's interior is obtainable.

In the case of isotopes, only a single isotope is generally used at one time, placed first in one guide, where all readings are taken in succession, then in the next guide, and so on. Different isotopes can be used but preferably not inserted simultaneously.

In FIG. 3 the three dimensional mapping is indicated as completed in the block 96. These data, along with a radiation prescription (98), i.e. desired dose and depth for the patient tissue surrounding the excision cavity, are used to calculate a radiation treatment plan 100. The calculation of the treatment plan takes into account the distance to the surface-located sensors and to the chest wall, in the case of a breast to be treated, since radiation must be limited at the skin to prevent damage, and also at the chest wall. The calculation will take this into account, lessening the depth of penetration of the total radiation in the regions of these locations. This is achieved far more easily using switchable x-ray sources, and preferably sources which are not only switchable on/off but also having voltage and current control.

With the treatment plan calculated, it is executed using the same sources and sensors, as indicated in the block 102. At this point the exterior sensors, outside the excision cavity, can be used to monitor radiation dose actually received. This can be used for emergency shutoff, for control of the procedure (including in real-time), or for verifying the actual treatment was according to plan.

Figure 6:
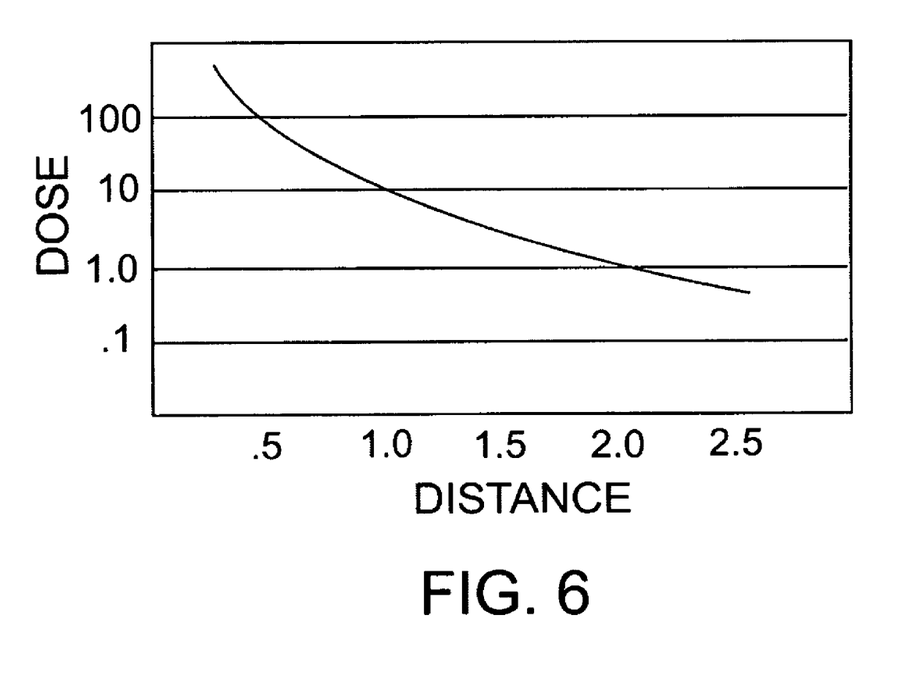
FIG. 6 is a graph showing radiation dose vs. distance from source.

FIGS. 6, 7, 7A and 7B demonstrate calculation of the shape of the cavity wall by the method described above. The chart in FIG. 6 represents the dose from an x-ray source operating at 45 $kV_p$. In FIG. 6, dose is indicated as a function of distance from the sensor. The vertical or y axis is a logarithmic scale. As indicated, dose falls off very rapidly with distance, not only due to the inverse square law ($1/r^2$) but also taking in the effects of attenuation of radiation passing through tissue absorption. For example, FIG. 6 shows that doubling the distance from the sensor, from about 0.5 cm to 1.0 cm, drops the dose approximately by a factor of nine, and from 1 cm to 2 cm, by an approximate factor of ten.

Figure 7:
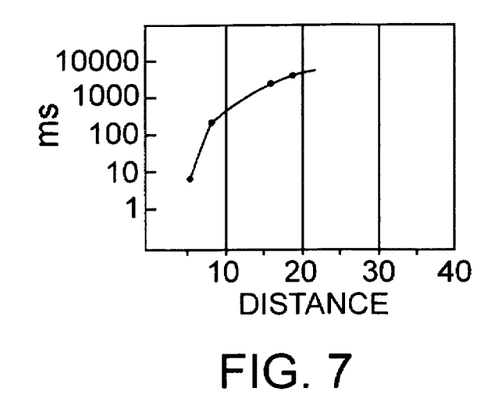
FIGS. 7, 7A and 7B are a graph, a schematic view and a table indicating relationship of distance to time required to receive a preselected dose, as well the relationship of simply distance to dose.
Figure 7A:
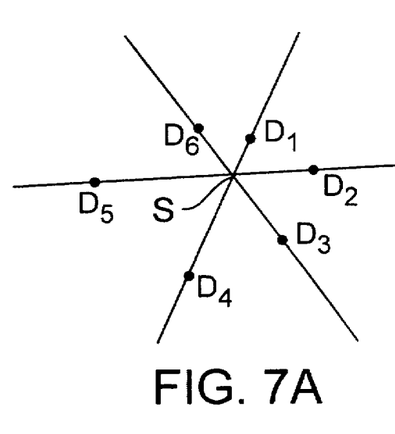
Figure 7B:
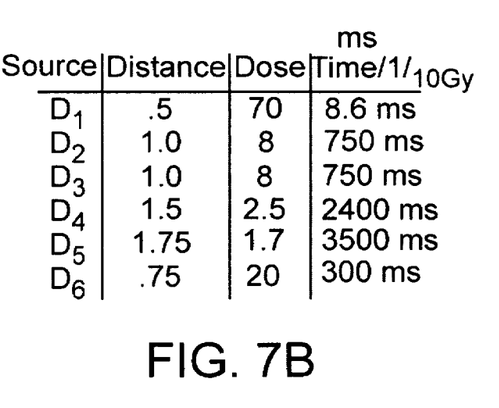

FIG. 7A schematically shows a possible transverse location of six different x-ray sources $D_1$ through $D_6$, in positions against the wall (not shown) of an arbitrary excision cavity. A sensor s is shown in a generally central position. As schematically indicated, each of the sources is a different difference from the sensor s. FIG. 7B shows an example of dose versus distance for the six sources $D_1$ through $D_6$. The information under "distance" and "dose" is as taken from the graph of FIG. 6. However, the right column in FIG. 7B corresponds to FIG. 7, which is the time duration to receive a specified dose, e.g. 0.16 Gy (as is well known 1 Gy=100 rad). FIG. 7 is a graph showing this form of distance mapping, with milliseconds (ms) on the vertical axis and distance (cm) on the horizontal axis. As discussed above, minimal radiation of the patient during mapping can be achieved by turning the switchable radiation sources to a high voltage setting and maintaining that setting for each source position, shutting off the source whenever a preselected dose is reached, such as 0.1 Gy. Note that 0.1 60 Gy, which is 10 rad, is a more than adequate level of radiation for detection by the central sensor and also sensors located outside the breast, as in FIG. 5. The graph of FIG. 7 illustrates how distance is determined, by an algorithm.

Returning to FIG. 5, the sensors s and s' are located on the surfaces of the breast and at the chest wall CW, to monitor radiation and also to locate the three dimensional cavity map relative to these locations. The surface mounted sensors s, as shown in FIG. 5, may fall within the prescribed volume to be treated. This is the case with the upper cavity $c_1$; the lower cavity $c_2$ has the chest wall sensor s' located within its prescription dose volume. During the mapping procedure, these sensors determine that the skin or chest wall is within the prescription dose region, and that the skin or the chest wall may receive a dose exceeding that desired by the physician. Excessive doses at these structures can lead to damage—in the case of the skin, poor outcome, and in the case of the chest wall, possible damage to lungs, heart, the great vessels and bone. Thus, the decision is made, either by the physician or the radiation oncologist, or by the computer program, as to whether the prescription dose should be maintained adjacent these structures or whether the potential for damage should dominate the treatment plan where necessary. With the switchable x-ray sources or their modulation preferred according to this invention, this issue is much more easily and more accurately handled. The x-ray sources can be switched on and off, and/or their voltage can be varied when nearing the surface, to lessen penetration. Moreover, the sensors s, s' can be used to monitor the treatment plan's accuracy and effectiveness, by measuring dose actually received at those structures during treatment. As noted above, voltage can be varied in real time during the treatment, in accordance with such detection.

In addition, and importantly, the sensors s and s' can be used to verify the total dose received in all regions, by calculation in the software which accurately extrapolates the total dose received at all locations. It is not necessary that a sensor be located directly in the prescription volume as in FIG. 5.

Figure 5A:
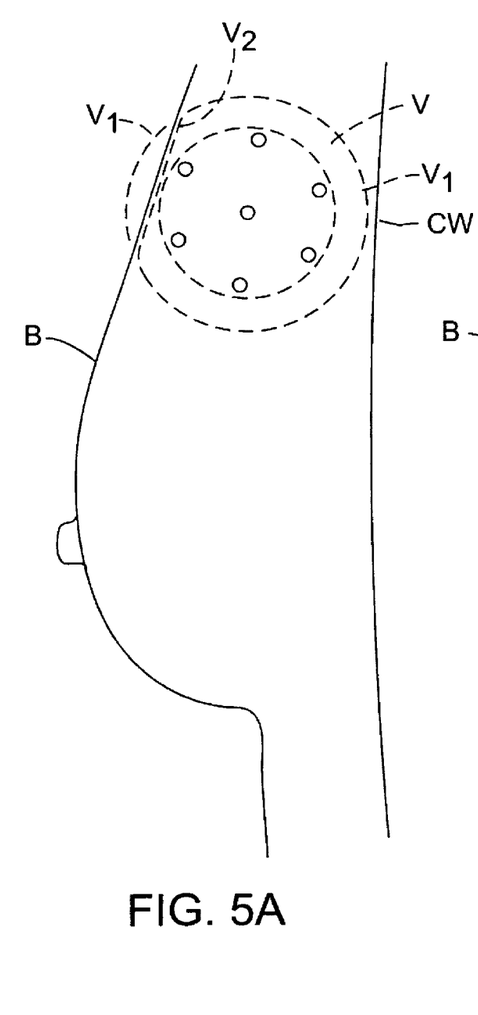
FIG. 5A is a schematic view showing a portion of FIG. 5 and showing a reduced dose of radiation at the skin which can be achieved with the invention.
Figure 5B:
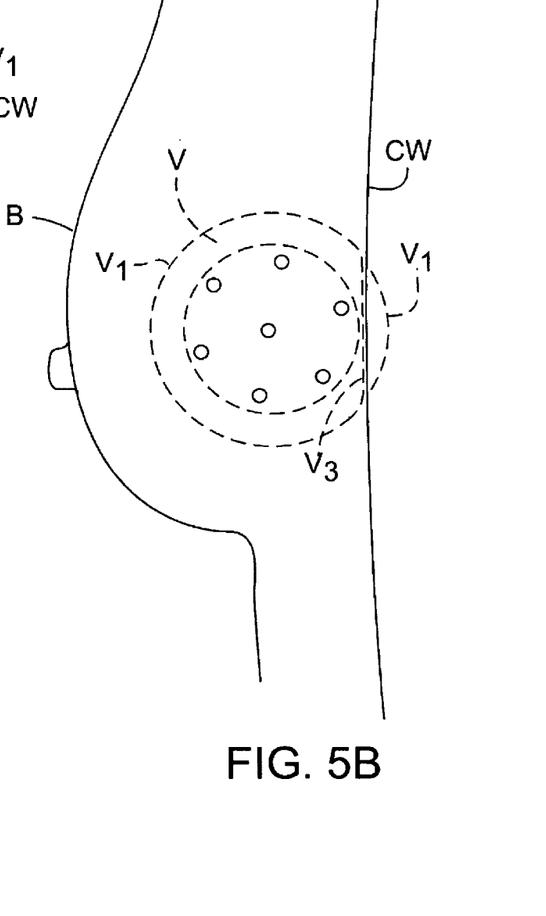
FIG. 5B is a view similar to FIG. 5A showing a reduced dose of radiation at the chest wall achievable with the invention.

FIGS. 5A and 5B demonstrate that use of switchable and variable sources, e.g. switchable x-ray tubes, enables far greater flexibility in treating a very specific, irregular prescription volume. Using the example of the breast, FIG. 5A again shows, as in FIG. 5, the situation where a prescription volume to be treated intersects with the exterior breast surface B. As explained, this is objectionable and often unacceptable with the potential to do severe damage to the skin. The dashed line $V_1$ defining this volume to be treated is an isodose curve, basically a three dimensional surface. A treatment plan must integrate the doses received from each of the many sources at all of the dwell points, optimizing the dose at every point within the volume to be treated and eliminating potentially damaging radiation at boundaries such as the breast surface.

FIG. 5A shows approximately what can be achieved using the invention and the preferred switchable, variable x-ray sources. Curve $V_1$ intersects with and passes outside the breast surface B. Here, however, the x-ray sources are switchable and variable as to at least voltage and preferably also current. The treatment plan algorithm takes this into account, along with dwell and position control, and optimizes, for all regions of the volume V to be treated, the dose that will be received, with the sources varied as to voltage for varying depth of penetration, and also as to either current or dwell time (current and dwell time are equivalent). The dwell time is varied by switching these sources on/off, while reduction of current is another way to reduce dose. The modified curve $V_2$ in FIG. 5A approaches very closely the skin, as is desired, such that virtually the entire volume V to be treated receives the prescription dose as nearly as possible, but without overdosing the skin or undergoing the regions near the intersection between the skin B and curve $V_1$ as would occur if only dwell time was varied at constant dose intensity. This greater control is achieved by a complex algorithm that calculates the treatment plan, with the ability to vary both dwell time (or current) and voltage (depth of penetration). In contrast, with radioactive sources, this is also a complex algorithm and is typically accomplished, as best possible. The isotope algorithm must take into account angles relative to each source, and the fall-off of dose with depth and with angle. The resulting adjusted dose curve under the skin, for example, is not as conformal as with the variable x-ray sources of the invention, however.

FIG. 5B, is a schematic view similar to FIG. 5A, but shows the situation near the chest wall rather than near the skin. The discussion above in regard to FIG. 5A also applies here.

As noted above, an algorithm for use with switchable, variable x-ray sources to achieve this complex prescription dose surface must involve the integration of the effects of all sources at all positions. Every dwell point of a source affects every point within the volume to be treated and surrounding points. If, for example, six sources (i.e. guides) are used in the applicator, and ten different dwell points are used in each guide, this produces sixty different dwell points, the effects of each of which must be integrated to the treatment plan as to the effect at every point reached by the radiation. This is a difficult problem but can be solved, with the appropriate algorithm, and the ability to achieve the desired treatment plan is made possible by the use of sources which are variable as to voltage, i.e. depth of dose.

The treatment described could be accomplished with continuous movement of the sources and sensor, with such movement taken into account in the algorithm and rate (or varying rates) of movement being a part of the treatment plan. It is also possible to perform three-dimensional mapping using moving sources, but this may be undesirable if the sources are continuously emitting radiation, since this can lead to excessive doses of radiation during mapping, or when mapping radiation is accumulated with treatment radiation. Development of more sensitive sensors could make moving mapping more desirable, with less radiation emitted. In the claims, references to moving the sources and sensor to a plurality or positions or locations, or references to taking readings at various locations should be understood to include continuous movement as well as intermittent motion.

It should also be understood that the calculation of a radiation treatment plan can take into account radiation already received during mapping in the volume to be treated. Once the cavity shape and location are determined, the radiation dose at each location, received during mapping, can be calculated and included in the prescription plan such that subsequent therapy is then the difference between the mapping dose and the total desired dose. If mapping dose is sufficiently small, however, this dose can generally be ignored.

Figure 8:
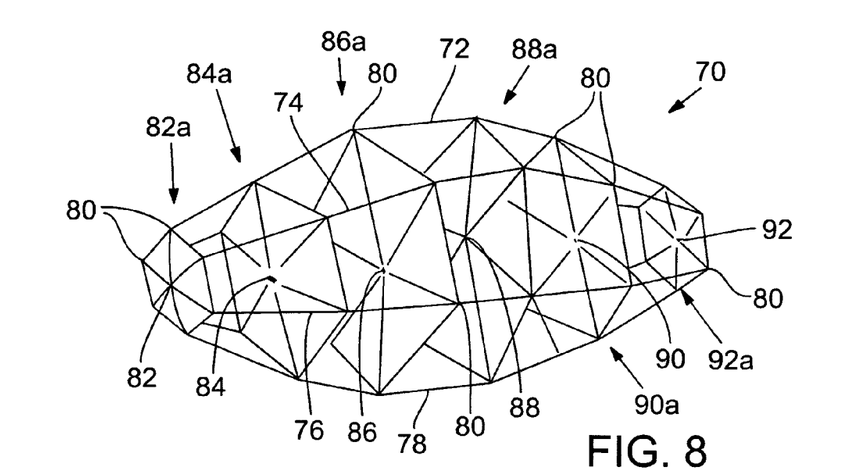
FIG. 8 is a schematic view in perspective, showing a wire-frame model resulting from mapping of an excision cavity in accordance with the invention.

FIG. 8 shows an example of a wire-frame type three dimensional map 70 that can be obtained using the mapping procedure of the invention. Outer longitudinal lines 72, 74, 76, 78, etc. of the wire frame model or three dimensional map represent the approximate positions of the guides in the cavity. Nodes 80 on each of the lines 72, 74, 76, etc. are at the locations of the guides where readings were taken from the sources there positioned, i.e. dwell points. The series of location points for the sensor are indicated at 82, 84, 86, 88, 90 and 92. The dwell points or nodes 80 are all in substantially the same plane with one of the sensor location points 82, 84, 86, etc. All measurements are taken one plane at a time, with the central measurement sensor and the x-ray sources within that same plane during that measurement. As noted earlier, in the case of isotopes typically only one isotope is used, positioned successively in each of the guides, so that each planar dwell point is within the same plane after all readings are taken for that plane. In other words, in each plane of measurement, the sources are advanced to the same point, such that they all lie in substantially the same plane with the sensor. Readings are taken sequentially rather than simultaneously, and for isotopes this involves repositioning to each of the different dwell points within each plane (although the order of the dwell points need not be to complete one plane before undertaking the next). For switchable sources, the series of sources preferably are simultaneously in place, but are sequentially turned on. It should be understood, however, that for switchable sources a single source could be used if desired, and for isotopes multiple sources could be used, although preferably not inserted into the excision cavity at the same time.

Each of the sensor points 82, 84, 86, etc. is roughly near the center of a plane, of which six such planes 82a, 84a, 86a, 88a, etc. are shown in FIG. 8, one for each reading location. It can be appreciated that merely having the data of the distance from the center or sensor point of each such wire plane to each of the plurality of surrounding points (six in the illustrated embodiment) will provide the dimensions of the plane, but will not locate that plane relative to the next and succeeding planes. One plane may be laterally displaced from the other planes, i.e., the sensor points 82, 84, 86, etc. may not be in a single line and perhaps not on a single smooth curve. Further, some of the planes could be rotated about the sensor point 82 or 84 or 86, etc. relative to other such planes, if the guides follow slightly tortuous paths. The additional data needed to locate these planes precisely relative to one another can be provided in one of two ways: by use of an applicator with a relatively rigid and linear central guide, and with peripheral guides that expand in a manner such that each particular curving guide lies in a single plane; or using data from the additional sensors placed outside the cavity, e.g. at the breast surface and along the chest wall, as described above. These additional sensors will provide distance data that will locate the planes relative to one another, and also locate the excision cavity itself (i.e. the wire frame model 70) within the breast or other patient tissue.

Figures 9, 10:
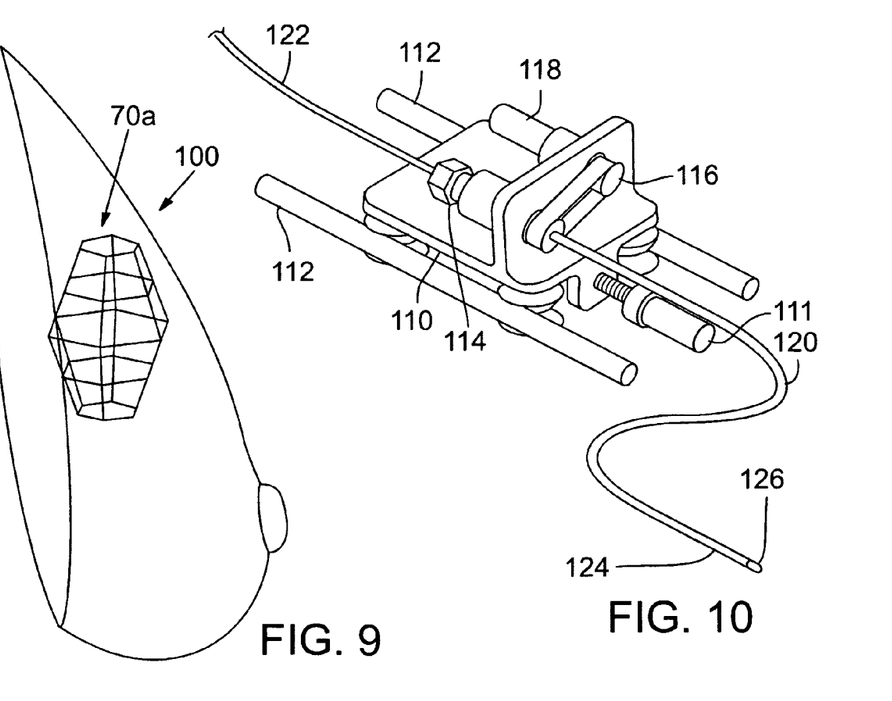
FIG. 9 is a schematic perspective view of a breast indicating an excision cavity in the form of a wire-frame map or model as in FIG. 8.
FIG. 10 is a schematic representation of a translation and rotation positioning mechanism for controlling a non-isotropic radiation source during delivery of brachytherapy.

FIG. 9 is similar to FIG. 8 but shows a three dimensional wire frame model as it might be located within a breast 100. The wire frame model is shown at 70a, oriented within the breast tissue. As in FIG. 5, the sensors can be located at the exterior of the breast and at the chest wall, not shown in FIG. 9.

The description above describes cavity mapping essentially on a spaced series of planes, more or less perpendicular to a central guide withing the cavity. This is an arbitrary choice, and other methodology may be used so long as the algorithm is fashioned to accommodate the node pattern selected. For example, another possible node pattern is helical and, in principle, nothing precludes even a random pattern so long as the node spacing on the cavity surface representation developed is adequate for the dose accuracy required.

In addition, the description above assumes the x-ray source or sources emit at least radially uniformly (transverse to their direction of translation) if not totally isotropically. As mentioned above, side emitting sources (emitting within a defined solid angle representing a portion of a more isotropic pattern) which are translated along the length of the guides as well as rotated with respect to the applicator and anatomy, can also be used. Again the treatment planning algorithm must be designed to create an optimized treatment plan using these additional degrees of freedom. This rotational, side-emitting embodiment would be particularly advantageous where the source is translated and rotated within a substantially central guide, rather than positioned in peripheral guides. Such an arrangement when modulated as it rotates, would emit in a manner reaching out to or retreating from irregular cavity surfaces and treatment plan requirements, adapting to radiation sensitive anatomic structures. References describing side emitting, miniature x-ray tubes are mentioned above.

Large, side-emitting, rotatable x-ray sources are known, but the methods producing rotation in these larger units are not very conducive to miniaturization and brachytherapy. With a miniature x-ray source fed by an electrical or fiber optic cable, it is preferable to translate and rotate the entire x-ray tube, winding up the cable and necessary utilities (e.g. cooling circuit) rather than devising high-voltage and fluid-transmitting rotary connections. The winding-up approach permits non-rotational connections which are reliable and well known in the industry, and at most requires perhaps extra cable length or revised cable design to accommodate the necessary rotation. Such rotation may be cumulative in one direction for the whole treatment plan, but advantageously would incorporate forward and backward rotation, minimizing "wind-up", but still accommodating the rotational coverage prescribed in the treatment plan. In principle, the extremes of rotation could be addressed by ±180° of motion. These problems can be solved easily by one of skill in the art.

Mechanical apparatus to provide controlled translation and rotation are well known, and many are available. One example is a sled on rails carrying a servo-driven rotary spindle on which is mounted the cable or catheter carrying the source to be positioned within the guide(s). Such an apparatus is shown schematically in FIG. 10. A sled 110 is riding on, and confined to rails 112, with its translation actuated by servo-motor 111. A rotary spindle and collet 114 is mounted on the sled 110 in bearings (not shown), and connected by a belt or gear drive 116 to a servo-motor 118. The collet is for gripping the catheter 120 so that it moves with the spindle. The servos 111 and 118 are responsive to the system controller (not shown) which manages delivery of the treatment plan. The spindle and collet 114 is connected to a catheter 120 into which the supply/utility cable 122 is positioned. On the distal end 124 of the cable 122 and catheter 120 is mounted the source 126. The assembled cable 122 and catheter 120 must resist length and rotational deflection to avoid error in delivery of the treatment plan. Length change can be controlled by inclusion of lengthwise reinforcing members having a high modulus, and rotation can be resisted by the methods of U.S. Pat. No. 4,425,919, both without giving up material bending flexibility. The apparatus described above is for the purpose of controlling one source. Similar apparatus can be fashioned to manage multiple sources.

The above described embodiments are intended to illustrate the principles of the invention, but not to limit its scope. Other embodiments and variations to this preferred embodiment will be apparent to those skilled in the art and may be made without departing from the spirit and scope of the invention as defined in the following claims.

We claim:

1. A method for intraoperative radiation therapy treatment in a living patient, comprising:

following excision of a tumor from a patient, while the patient remains under anesthesia, mapping the excision cavity by the steps of:

(a) inserting an applicator into the excision cavity, the applicator including a series of guides, (b) before or after step (a), inserting one or more radiation sensors into peripheral ones of the guides and inserting an ionizing radiation source into a central one of the guides, (c) expanding the applicator to substantially fill the cavity, thereby placing the peripheral guides substantially at walls of the cavity adjacent to a volume to be treated with radiation, (d) moving the source and sensors through the guides and taking a reading with the sensor for each of a plurality of locations of the sensors along such movement, such locations being sufficient to substantially define the shape of the walls of the cavity, (e) from data determined in step (d), determining a three-dimensional model of the excision cavity, using a radiation prescription prepared by an attending physician, making a radiation treatment plan for a volume to be treated immediately surrounding the excision cavity based on the three-dimensional model of the cavity, while the patient remains under anesthesia and the applicator remains within the incision cavity, for irradiation of the volume to be treated by use of such ionizing radiation sources and the applicator, and executing the treatment plan by moving the ionizing radiation source through the central guide of the applicator with appropriate dwell times such that substantially the prescribed dose of radiation is received in all regions of the volume to be treated.

2. The method of claim 1, wherein the ionizing radiation source is a switchable x-ray source.

3. The method of claim 2, wherein the switchable x-ray source during execution of the treatment plan is varied in voltage to adjust depth of x-ray penetration at different locations.

4. The method of claim 1, wherein the ionizing radiation source is an isotope, which is removed after mapping and reinserted into the applicator for execution of the treatment plan.

5. The method of claim 1, further including obtaining pathology from the excised tumor, and, if a clean margin is not indicated, re-excising before mapping the excision cavity, all while the patient remains under anesthesia.

6. The method of claim 5, wherein the step of obtaining pathology from the tumor comprises use of a rapid method of pathology determination.

7. The method of claim 1, wherein the ionizing radiation source is a switchable x-ray source, and wherein step (d), taking a reading with the sensors, is accomplished by operating the source at a high voltage level and measuring, via the sensors, the duration of time required for the sensors to detect a preselected dose from the source at each location.

8. The method of claim 1, wherein step (d), taking a reading with the sensors, is accomplished by determining dose received at the sensors from the source over a preselected period of time.

9. The method of claim 1, wherein prior to mapping of the cavity, extra-cavity sensors are placed outside the cavity in critical areas where radiation dose must be limited to avoid damage, and during mapping of the excision cavity, readings are taken at each extra-cavity sensor, and data from such readings are used to modify the radiation treatment plan so as to limit dose as needed in such critical areas.

10. The method of claim 9, further including, during execution of the treatment plan, monitoring dose actually received at such extra-cavity sensors to assure that dose is limited as needed in the critical areas.

11. A method for three-dimensional mapping of a cavity in a human body, comprising:
  (a) inserting an applicator into the cavity, the applicator including a series of guides, including peripheral guides and a generally central guide,
  (b) expanding the applicator to substantially fill the cavity, thereby placing the peripheral guides substantially at walls of the cavity adjacent to a volume to be treated with radiation,
  (c) with one or more ionizing radiation sources in one or more of the guides and with a radiation sensor in one or more of the guides, such that one of a sensor and a source is in a generally central guide and the other is in at least one peripheral guide, moving the source and sensor through the guides and taking a reading with the sensor for each of a series of positions in the peripheral guide, along such movement, such locations being sufficient to substantially define the shape of the walls of the cavity,
  (d) from data determined in step (c), determining a three-dimensional model of the cavity.

12. The method of claim 11, wherein the ionizing radiation sources are switchable x-ray sources, and wherein step {circle around (c)}, taking a reading with the sensor, is accomplished by operating the sources at a high voltage level and measuring, via the sensor, the duration of time required for the sensor to detect a preselected dose for each source at each location.

13. A method for radiation therapy treatment of a patient, comprising:
  (a) inserting an applicator into a cavity in the patient's body, the applicator including a series of guides, including peripheral guides and a generally central guide,
  (b) expanding the applicator to substantially fill the cavity, thereby placing peripheral guides substantially at walls of the cavity adjacent to a volume to be treated with radiation,
  (c) with one or more ionizing radiation sources in one or more of the guides and with a radiation sensor in one or more of the guides, such that one of a sensor and a source is in a generally central guide and the other is in at least one peripheral guide, moving the source and sensor through the guides and taking a reading with the sensor for each of a series of positions in the peripheral guide, along such movement, such locations being sufficient to substantially define the shape of the walls of the cavity,
  (d) from data determined in step {circle around (c)}, determining a three-dimensional model of the cavity,
  (e) making a radiation treatment plan for a volume to be treated immediately surrounding the cavity based on a radiation prescription and on the three-dimensional model of the cavity, for irradiation of the volume to be treated by use of such ionizing radiation sources and the applicator, and
  (f) executing the treatment plan by moving the ionizing radiation source through one or more guides of the applicator with appropriate dwell times such that substantially prescribed dose of radiation is received in all regions of the volume to be treated.

14. The method of claim 13, further including placing extra-cavity sensors outside the cavity in critical areas where radiation dose must be limited to avoid damage, and during execution of the treatment plan, monitoring dose received at such extra-cavity sensors to assure that dose is limited in the critical areas.

15. The method of claim 13, wherein the x-ray source is capable of emitting radiation directionally, and the method including rotating the x-ray source in the applicator guide, and varying voltage for different rotational positions with the source emitting radiation rotationally, so as to achieve different radiation depth penetration at different rotational positions in the tissue.

16. A method for treating with x-ray radiation a volume within a living patient while avoiding damage to sensitive areas and limiting radiation dose where needed, comprising:
  (a) placing a plurality of x-ray sensors adjacent to the volume to be treated, in an applicator,
  (b) placing a switchable x-ray source at a generally central location in the applicator so as to be generally surrounded by the sensors,
  (c) calibrating the plurality of x-ray sensors by switching the source on and off in turn, with the sensors clustered closely around the source, and determining the dose read at each of the x-ray sensors,
  (d) expanding the applicator within the volume to be treated, so as to spread the array of sensors outwardly as the applicator expands, thus spacing each sensor generally radially away from the source, (e) placing additional x-ray sensors outside the volume to be treated, so as to monitor x-ray radiation received at various sites outside the volume to be treated, (f) moving the x-ray source and the sensors through the volume to be treated, turning the x-ray source on and off in turn, and detecting the radiation from the source using the x-ray sensor at a series of different positions within the volume, (g) calculating the relative positions of all of the x-ray sensors and the x-ray source using information obtained from step (f), (h) making a treatment plan for the volume to be treated, based on x-ray radiation dose prescribed for various regions of the volume to be treated, and including a plan for moving the x-ray source and the sensors to different positions along the volume to be treated, with on/off switching of the source as needed, along the path of movement for the treatment plan, (i) executing the treatment plan by moving the x-ray source and sensors through the volume to be treated, in accordance with the treatment plan, and controlling x-ray delivery from the x-ray source in accordance with the treatment plan, including switching the source on and off as needed.

17. The method of claim 16, wherein the x-ray source is capable of emitting radiation directionally, and the method including rotating the x-ray source in the applicator guide, and varying voltage for different rotational positions with the source emitting radiation directionally, so as to achieve different radiation depth penetration at different rotational positions in the tissue.

18. The method of claim 16, wherein the source is modulated during treatment.

19. A method used in brachytherapy radiation treatment, to closely achieve a prescription radiation dose in a patient's tissue, comprising:

positioning an applicator in a cavity or other location in the patient's tissue, moving an electronic x-ray source axially through a guide in the applicator and thus progressing the x-ray radiation through the tissue, either continuously or in steps, and applying a prescription radiation dose by varying voltage to the electronic x-ray source as the source advances through the applicator guide so as to vary the depth of penetration of x-ray radiation into tissue at different locations in the tissue.

20. The method of claim 19, further including varying current in the electronic x-ray source for different positions along the applicator guide.

21. The method of claim 19, wherein the movement of the x-ray source is in steps, to a series of dwell positions, and including varying voltage within a single dwell position.

22. The method of claim 19, wherein the x-ray source emits radiation directionally, and the method including rotating the x-ray source in the applicator guide, and varying voltage for different rotational positions with the source emitting radiation directionally, so as to achieve different radiation depth penetration at different rotational positions in the tissue.

23. A method used in brachytherapy radiation treatment, to closely achieve a prescription radiation dose in a patient's tissue, comprising:

positioning an applicator in a cavity or other location in the patient's tissue, moving an electronic x-ray source axially through a guide in the applicator and thus progressing the x-ray radiation through the tissue, either continuously or in steps, applying a prescription radiation dose by varying voltage to the electronic x-ray source as the source advances through the applicator guide so as to vary the depth of penetration of x-ray radiation into tissue at different locations in the tissue, and controlling dose intensity by one of, varying current in the electronic x-ray source for different positions along the applicator guide, and varying dwell time of the electronic x-ray source for different positions along the applicator guide.

24. The method of claim 23, wherein the movement of the x-ray source is in steps, to a series of dwell positions, and including varying voltage within a single dwell position.

25. The method of claim 23, wherein the x-ray source is emits radiation directionally, and the method including rotating the x-ray source in the applicator guide, and varying voltage for different rotational positions with the source emitting radiation directionally, so as to achieve different radiation depth penetration at different rotational positions in the tissue.

26. A method used in brachytherapy radiation treatment, to closely achieve a prescription radiation dose in a patient's tissue, comprising:

positioning an applicator in a cavity or other location in the patient's tissue, making a radiation treatment plan for a volume to be treated immediately surrounding the cavity based on a radiation prescription for irradiation of the volume to be treated by use of an electronic x-ray source, executing the treatment plan by moving the electronic x-ray source axially through a guide in the applicator and thus progressing the x-ray radiation through the tissue with appropriate dwell times such that a prescribed dose of radiation is received in all regions of the volume to be treated, and controlling the prescription radiation dose by varying voltage to the electronic x-ray source as the source advances through the applicator guide so as to vary the depth of penetration of x-ray radiation into tissue at different locations in the tissue.

27. The method of claim 26 further including varying current in the electronic x-ray source for different positions along the applicator guide to control dose intensity.

28. The method of claim 26, wherein the x-ray source is emits radiation directionally, and the method including rotating the x-ray source in the applicator guide, and varying voltage for different rotational positions with the source emitting radiation directionally, so as to achieve different radiation depth penetration at different rotational positions in the tissue.

* * * * *